(12) United States Patent
Kim et al.

(10) Patent No.: US 12,061,192 B2
(45) Date of Patent: Aug. 13, 2024

(54) CHOLESTEROL MEASUREMENT DEVICE

(71) Applicant: GREEN CROSS MEDICAL SCIENCE, Yongin-si (KR)

(72) Inventors: Hyu Jeong Kim, Yongin-si (KR); Eun Myung Shin, Yongin-si (KR); Jung Sub Shin, Yongin-si (KR); Dong Han Kim, Yongin-si (KR); Soon Min Hong, Yongin-si (KR)

(73) Assignee: GREEN CROSS MEDICAL SCIENCE, Yongin-si (KR)

( * ) Notice: Subject to any disclaimer, the term of this patent is extended or adjusted under 35 U.S.C. 154(b) by 642 days.

(21) Appl. No.: 17/287,370

(22) PCT Filed: Nov. 7, 2019

(86) PCT No.: PCT/KR2019/015066
§ 371 (c)(1),
(2) Date: Apr. 21, 2021

(87) PCT Pub. No.: WO2020/096373
PCT Pub. Date: May 14, 2020

(65) Prior Publication Data
US 2021/0341465 A1    Nov. 4, 2021

(30) Foreign Application Priority Data

Nov. 8, 2018   (KR) .................. 10-2018-0136792
Nov. 8, 2018   (KR) .................. 10-2018-0136874

(51) Int. Cl.
*G01N 21/47*    (2006.01)
*G01N 21/25*    (2006.01)
(Continued)

(52) U.S. Cl.
CPC ............ *G01N 33/526* (2013.01); *G01N 21/25* (2013.01); *G01N 21/47* (2013.01); *G01N 33/92* (2013.01)

(58) Field of Classification Search
CPC ...... G01N 33/526; G01N 21/25; G01N 21/47; G01N 33/92; G01N 33/52;
(Continued)

(56) References Cited

U.S. PATENT DOCUMENTS 5,120,507 A   6/1992   Sano et al.
5,780,304 A   7/1998   Matzinger et al.
(Continued)

FOREIGN PATENT DOCUMENTS

CN   101430286 A   5/2009
CN   101686803 A   3/2010
(Continued)

OTHER PUBLICATIONS

International Searching Authority, International Search Report for PCT/KR2019/015066 dated Feb. 19, 2020 [PCT/ISA/210].
(Continued)

*Primary Examiner* — Michelle M Iacoletti
*Assistant Examiner* — Judy Dao Tran
(74) *Attorney, Agent, or Firm* — Sughrue Mion, PLLC

(57) ABSTRACT

A cholesterol measurement device includes a measuring instrument body; and a light-intensity check member mounted on and integrated with the measuring instrument body. The light intensity check member reflects light emitted from a light-emitting unit, allowing detecting abnormal light intensity and accurate assessing light intensity change, which prevents a measurement value change due to the change in light intensity and improves reliability of the measurement value. The device keeps a measurement unit clean all the time since the measurement unit can be easily (Continued)

cleaned by separating a strip fixation unit, when a specimen flows into the strip fixation unit in which a measurement strip is inserted.

11 Claims, 9 Drawing Sheets

(51) Int. Cl.
*G01N 33/52* (2006.01)
*G01N 33/92* (2006.01)

(58) Field of Classification Search
CPC ... G01N 2021/7759; G01N 2021/7773; G01N 21/78; G01N 21/8483
See application file for complete search history.

(56) References Cited

U.S. PATENT DOCUMENTS

| | | | |
|---|---|---|---|
| 6,239,445 B1* | 5/2001 | Shaeef | G01N 21/8483 250/576 |
| 7,118,713 B2* | 10/2006 | Brock | G01N 21/78 422/566 |
| 2004/0247491 A1 | 12/2004 | Brock et al. | |
| 2006/0243031 A1 | 11/2006 | Kondo et al. | |
| 2010/0311091 A1 | 12/2010 | Bae et al. | |
| 2010/0331636 A1 | 12/2010 | Hübner et al. | |
| 2014/0271362 A1 | 9/2014 | Markovsky et al. | |
| 2015/0160134 A1* | 6/2015 | Booker | G01N 21/278 422/403 |
| 2015/0204811 A1 | 7/2015 | Kim et al. | |
| 2015/0355681 A1* | 12/2015 | Chen | H05K 5/023 361/679.56 |
| 2016/0242683 A1* | 8/2016 | Ishiguro | A61B 5/14532 |
| 2016/0370366 A1* | 12/2016 | Fleming | B01L 3/502746 |

FOREIGN PATENT DOCUMENTS

| | | | | |
|---|---|---|---|---|
| CN | 103124903 A | | 5/2013 | |
| DE | 84 11 914 U1 | | 7/1984 | |
| EP | 1965199 A1 | * | 9/2008 | ......... G01N 21/4738 |
| JP | 62-12856 A | | 1/1987 | |
| JP | 08-043387 A | | 2/1996 | |
| JP | 08-320288 A | | 12/1996 | |
| JP | H 08320288 A | * | 9/2002 | ............ G01N 21/01 |
| JP | 2006-526780 A | | 11/2006 | |
| JP | 10-2010-0130903 A | | 12/2010 | |
| JP | 10-2016-0086119 A | | 7/2016 | |
| KR | 10-2015-0053544 A | | 5/2015 | |
| KR | 20190058821 A | * | 11/2017 | ............... G01N 1/28 |

OTHER PUBLICATIONS

International Searching Authority, Written Opinion for PCT/KR2019/015066 dated Feb. 19, 2020 [PCT/ISA/237].

* cited by examiner

CHOLESTEROL MEASUREMENT DEVICE

CROSS REFERENCE TO RELATED APPLICATIONS

This application is a National Stage of International Application No. PCT/KR2019/015066 filed Nov. 7, 2019, which claims priority based on Korean Patent Application No. 10-2018-0136874 filed on Nov. 8, 2018 and Korean Patent Application No. 10-2018-0136792 filed on Nov. 8, 2018, the entire contents of which are incorporated herein by reference.

TECHNICAL FIELD

The present invention relates to a cholesterol measurement device, and more particularly, to a cholesterol measurement device using a color development method that changes the color development of a measurement strip.

BACKGROUND ART

The quantity of total cholesterol in serum, plasma, or blood is known as one of indicators of indicating the risk of coronary arteriosclerosis. As a result, through analysis of the concentration of blood cholesterol, the occurrence and possibility of diseases such as arteriosclerosis have been diagnosed and prevented.

Methods of measuring cholesterol include an electrochemical method which measures a change in electrical resistance value according to the quantity of a cholesterol component, a color development method which measures the degree of change by changing the color development of a strip, and the like.

In the case of a cholesterol measurement device using a color development method that measures a level of color development of the strip to measure blood cholesterol, a measuring instrument body emits light of LED with a specific wavelength band on a color developed portion according to a color developed from the measurement strip and then a photo diode (PD) detects the intensity of reflected light. At this time, the intensity of reflected light is changed according to the degree of color development of a reflective surface of a check strip and the intensity of emitted light.

In other words, the cholesterol measurement device using the color development method emits light with an LED on the measurement strip, and the photo diode (PD) detects the intensity of light reflected by the measurement strip to measure the quantity of cholesterol in a specimen.

The cholesterol measurement device using the color development method initially sets the emitted intensity of LED light through calibration to be constant, but the deterioration of the LED component occurs according to the quantity of use over time, and as a result, a phenomenon of decreasing the intensity of light emitted from the LED may occur.

In addition, when the intensity of light emitted from the LED is changed, the measurement value may be changed when cholesterol is actually measured, and it is impossible to trust the measured value. Therefore, the LED of the measuring instrument should always emit a constant intensity of light, or check whether the constant intensity of light is emitted.

In order to perform this operation, each measuring instrument manufacturer provides a check strip with a specific gray value, and should perform an operation of generating an error message or re-controlling the intensity of emitted light of the LED by determining that the intensity of light emitted from the LED has been changed out of a measurement value of a desired section when a reflection value of the strip is measured by the check strip.

However, since the check strip used in the conventional cholesterol measurement device using the color development method is provided by each manufacturer separately from the measuring instrument body, there is a problem that the check strip is lost during use.

In addition, since the conventional check strip is formed of an injection molding product, there is a problem in that a deviation in gray value between the check strips occurs.

In addition, before measuring cholesterol every day, it is necessary to check whether the intensity of LED light is abnormal by measuring cholesterol with the check strip, but there are many cases where it is difficult to force or confirm this check to the user, so that it is not possible to actually check a change in LED light intensity, and there is a problem in that the accuracy of cholesterol measurement is not secured because the change in LED light intensity is not checked.

On the other hand, a specimen of blood or serum is dropped into a specimen inlet of the measurement strip, but at this time, when the specimen is dropped out of the specimen inlet or a dose or more of specimen is dropped in the specimen inlet due to a user's mistake, the specimen overflows into a measurement window of the measuring instrument body, not the measurement strip.

When the specimen overflows into the measurement window, the measurement unit of the cholesterol measuring instrument is contaminated, and as a result, contaminants need to be quickly removed from the measuring instrument, but the specimen is inserted between the measurement strip and a strip fixation device into which the measurement strip is inserted, and thus, there was a problem in that it is not easy to clean the measuring instrument.

In addition, as the case where the specimen is dropped out of the outside of the measurement strip is repeated, the specimen is solidified in the strip fixation device, and as a result, in some cases, the measurement strip is not inserted.

Meanwhile, in order to record the values measured by the cholesterol measurement device, there are methods of transcribing and printing the values displayed on an LCD, etc. In the transcribing method, since there is a possibility of writing an incorrect value due to a typing error, the measured value is printed using a printer to be confirmed.

In the conventional cholesterol measurement device, there is an inconvenience that a printer device of printing the measurement value needs to be connected wirelessly or wiredly to the cholesterol measurement device, and needs to be carried separately.

PRIOR ART DOCUMENTS

Patent Document (Prior Patent) Korean Patent Publication No. 2016-0086119, 'Cholesterol measurement device and method thereof' (Jul. 19, 2016)

DISCLOSURE

Technical Problem

An object of the present invention is to provide a cholesterol measurement device capable of having no fear of loss and solving an inconvenience to store a check strip separately by changing a check strip of confirming whether the intensity of light is abnormal into a block shape to be provided integrally with a measuring instrument body.

Another object of the present invention is to provide a cholesterol measurement device capable of solving problems caused by a deviation of a check strip when a light-intensity check member of confirming whether the light intensity is abnormal is integrally provided to inspect whether the light intensity is abnormal.

Yet another object of the present invention is to provide a cholesterol measurement device capable of ensuring the accuracy of cholesterol measurement by automatically confirming everyday whether the light intensity is abnormal.

Another object of the present invention is to provide a cholesterol measurement device capable of cleaning a measurement unit by separating a strip fixation unit into which a measurement strip is inserted to clean the measurement unit.

Another object of the present invention is to provide a cholesterol measurement device capable of cleaning a measurement unit by easily cleaning the measurement unit to ensure reliability when measuring cholesterol and improve the measurement accuracy.

Yet another object of the present invention is to provide a cholesterol measurement device including a printer which is detachable from a measuring instrument body and portable.

Technical Solution

In order to achieve the objects, an embodiment of the present invention provides a cholesterol measurement device including: a measuring instrument body which includes a measurement unit where a measurement strip is positioned and a light-emitting unit emitting light to the measurement unit and detects the intensity of light reflecting after emitting the light to the measurement strip to measure the quantity of cholesterol; and a light-intensity check member which is mounted and integrally provided on the measuring instrument body and reflects the light emitted from the light-emitting unit to check whether the intensity of light is abnormal.

In the present invention, the light-intensity check member may have a block shape having a flat lower surface.

In an embodiment of the present invention, the cholesterol measurement device may further include a spring member elastically supporting the light-intensity check member.

In the present invention, a measurement window member through which the light emitted from the light-emitting unit passes may be positioned in the measurement unit, and the light-intensity check member may be elastically supported by the spring member to be positioned in close contact with the measurement window member.

In the present invention, the measuring instrument body may include a body housing member of which the measurement unit where the measurement strip is positioned is provided at one side and the light-emitting unit emitting the light to the measurement unit is provided therein; and an opening/closing member opening and closing the measurement unit, and the light-intensity check member may be positioned on a lower surface of the opening/closing member.

In the present invention, a measurement window member through which the light emitted from the light-emitting unit passes may be positioned in the measurement unit, and the light-intensity check member may be elastically supported by a spring member in the state where the opening/closing member is closed, and be positioned in close contact with the measurement window member.

In the present invention, a strip inlet may be positioned at one side of the opening/closing member so that the measurement strip can be inserted between the light-intensity check member and the measurement window member in the state where the opening/closing member is closed, and the light-intensity check member may have an inclined surface which is positioned at a front end side positioned toward the strip inlet to guide the insertion of the measurement strip.

In the present invention, the measuring instrument body may include a real time clock (RTC), and include a light-intensity abnormality checking unit which checks whether a date has changed when power is turned ON, operates the light-emitting unit when the date is changed to emit the light to the light-intensity check member, and checks whether the light-emitting unit is abnormal by the light reflected by the light-intensity check member.

An embodiment of the present invention may provide the cholesterol measurement device capable of cleaning the measurement unit by including a strip fixation unit to which the measurement strip is inserted and detachably coupled, which is detachable from the measuring instrument body, and a coupling unit for the strip fixation unit which is mounted and positioned on the measuring instrument body and is detachably coupled with the strip fixation unit.

In the present invention, the strip fixation unit may include strip side support members which are spaced apart from each other so that the measurement strip is inserted therebetween and support both sides of the measurement strip; and a strip front-end support member which has both end sides which are connected to one end side of the pair of spaced strip side support members and supports a front-end of the measurement strip, wherein a first slide coupling groove may be positioned in a longitudinal direction at any one side of an outer side of the measurement strip and an inner side of the strip side support member, and a first slide rail unit inserted into the first slide coupling groove may be positioned to protrude at the other side of the outer side of the measurement strip and the inner side of the strip side support member.

In the present invention, the coupling unit for the strip fixation unit may include side support members for strip fixation unit spaced apart from each other to support the outer sides of the strip side support members of the strip fixation unit; and a front support member for strip fixation unit supporting the outer side of the strip front-end support member, a second slide coupling groove may be positioned at any one side of an inner side of the side support member for strip fixation unit and an outer side of the strip side support member, and a second slide rail unit may be positioned at the other side of the inner side of the side support member for strip fixation unit and the outer side of the strip side support member to be inserted into the second slide coupling groove and slided.

In the present invention, the outer side of the strip side support member of the strip fixation unit and the inner side of the side support member for strip fixation unit of the coupling unit for the strip fixation unit may have a spacing of at least 0.01 mm to 2.0 mm.

The spacing may be filled by the outer side of the strip side support member while the strip side support member is elastically modified when the measurement strip is inserted into the strip fixation unit.

In the present invention, a width of the measurement strip may be formed to be larger by 0.02 mm to 4.0 mm than the spacing between the inner sides of the strip side support members corresponding thereto.

In the present invention, a coupling guide groove may be positioned at any one side of the inner side of the front support member for strip fixation unit and the outer side of the strip front-end support member, and a coupling guide rail unit inserted into the coupling guide groove may be positioned to protrude at the other side of the inner side of the front support member for strip fixation unit and the outer side of the strip front-end support member.

In the present invention, the measurement unit may further include a fixation locking unit capable of locking the position of the strip fixation unit coupled to the coupling unit for the strip fixation unit.

In the present invention, the fixation locking unit may include a first locking unit positioned at the rear end side of the strip fixation unit; and a second locking unit positioned at the rear end side of the coupling unit for the strip fixation unit and positioned to be locked with the first locking unit.

In the present invention, the second locking unit includes a locking groove formed on the lower surface of the coupling unit for the strip fixation unit, and the first locking unit may include a wedge-shaped locking step which is inserted to the locking groove at an end side thereof, and an elastic support member that elastically supports and presses the locking step to separate the locking step from the locking groove.

In the present invention, a pressing groove indicating a pressing position of the elastic support member may be positioned on the upper surface of the elastic support member, and the elastic support member may descend when a portion where the pressing groove is positioned is pressed so that the locking step may be separated from the locking groove.

In an embodiment of the present invention, the cholesterol measurement device may further include a printer body which is detachably coupled with the measuring instrument body and electrically connected with the measuring instrument body to print a result of cholesterol measurement values measured by the measuring instrument body and is embedded with a rechargeable battery.

In the present invention, the locking member for locking and fixing the measuring instrument body is positioned to protrude on the measuring instrument seating unit of the printer body and the locking member may have a ¬-shaped shape and protrude on the measuring instrument seating unit so that a bent end side is positioned at the rear side. A first locking insertion unit into which the locking member is inserted and locked may be positioned on the lower surface of the measuring instrument body, a second locking insertion unit into which a bent end side of the locking member is inserted may be positioned in the first locking insertion unit, and a moving member may be positioned in the measuring instrument seating unit to support the rear end of the measuring instrument body and be pushed toward the rear end of the measuring instrument body, and be elastically supported to return to its original position.

Advantageous Effects

According to the present invention, there are effects of having no fear of loss and solving an inconvenience to store the check strip separately to improve a convenience in use by changing the check strip of confirming whether the quality of light is abnormal into a block shape to be provided integrally with the measuring instrument body.

According to the present invention, there are effects of solving the problems caused by a deviation in the check strip when the light-intensity check member of confirming whether the intensity of LED light is abnormal is integrally provided to inspect whether the light intensity is abnormal, accurately confirming a change in light intensity to prevent a change in measurement value according to the change in light intensity, and improving the reliability to the measurement value.

According to the present invention, there are effects of improving the accuracy of the measurement value during measurement and securing the reliability of the measurement value by automatically checking every day whether the light intensity is abnormal.

According to the present invention, there are effects of improving a convenience during cleaning and keeping the measurement unit clean at all times by separating the strip fixation unit when a specimen flows into the strip fixation unit into which the measurement strip is inserted to easily clean the measurement unit.

According to the present invention, there are effects of improving the accuracy of the measurement value when measuring cholesterol and securing the reliability of the measurement value by easily cleaning the measurement unit.

According to the present invention, there is an effect of greatly improving a convenience in use by including a printer which is detachable from the measuring instrument body and portable to output a measurement value directly in use and confirm the measurement value.

DESCRIPTION OF DRAWINGS

FIG. 6 is a cross-sectional view before a measurement strip is inserted and coupled into a strip fixation unit, and FIG. 7 is a cross-sectional view illustrating a state in which the measurement strip is inserted and coupled into the strip fixation unit.

BEST MODE

Figure 1:
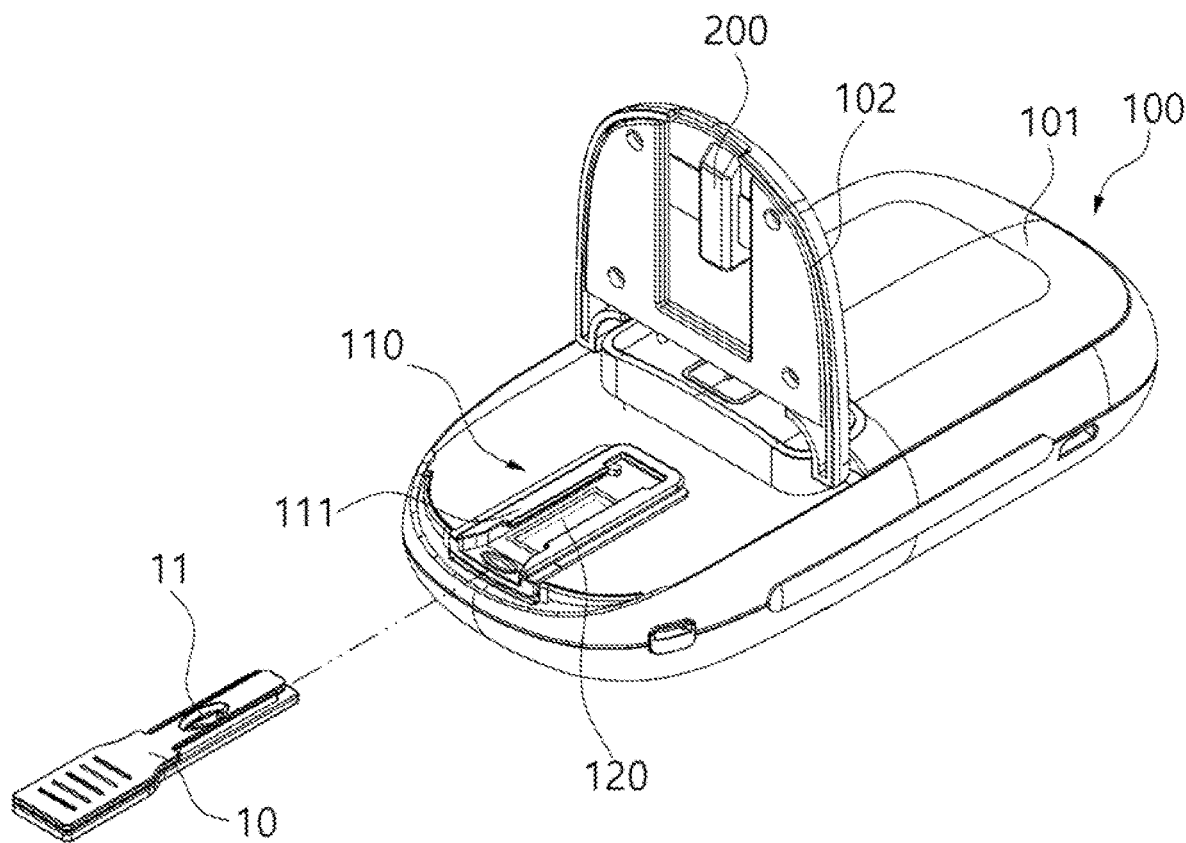
FIG. 1 is a perspective view illustrating an embodiment of a cholesterol measurement device according to the present invention.
Figure 2:
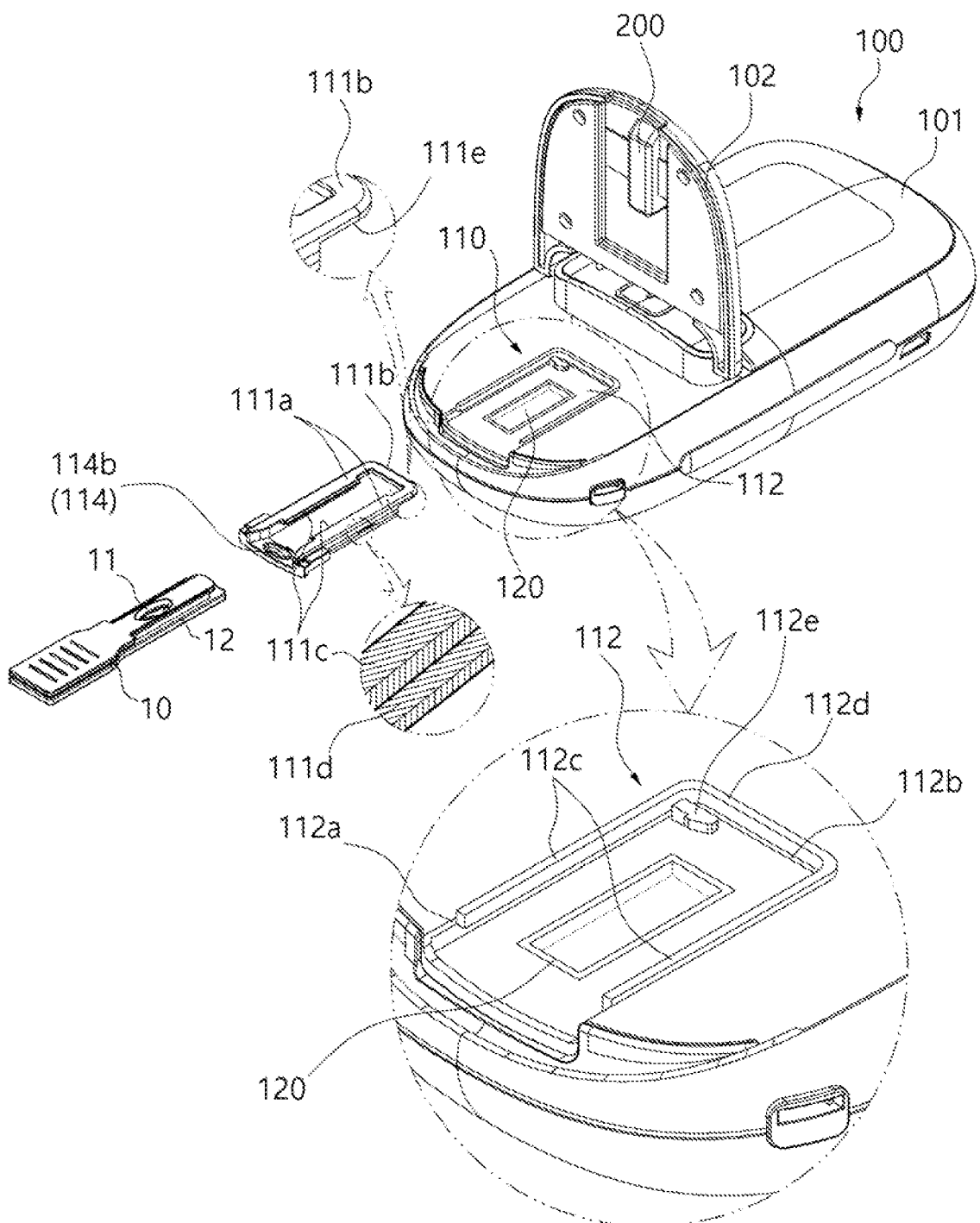
FIG. 2 is an exploded perspective view illustrating an embodiment of the cholesterol measurement device according to the present invention.
Figure 3:
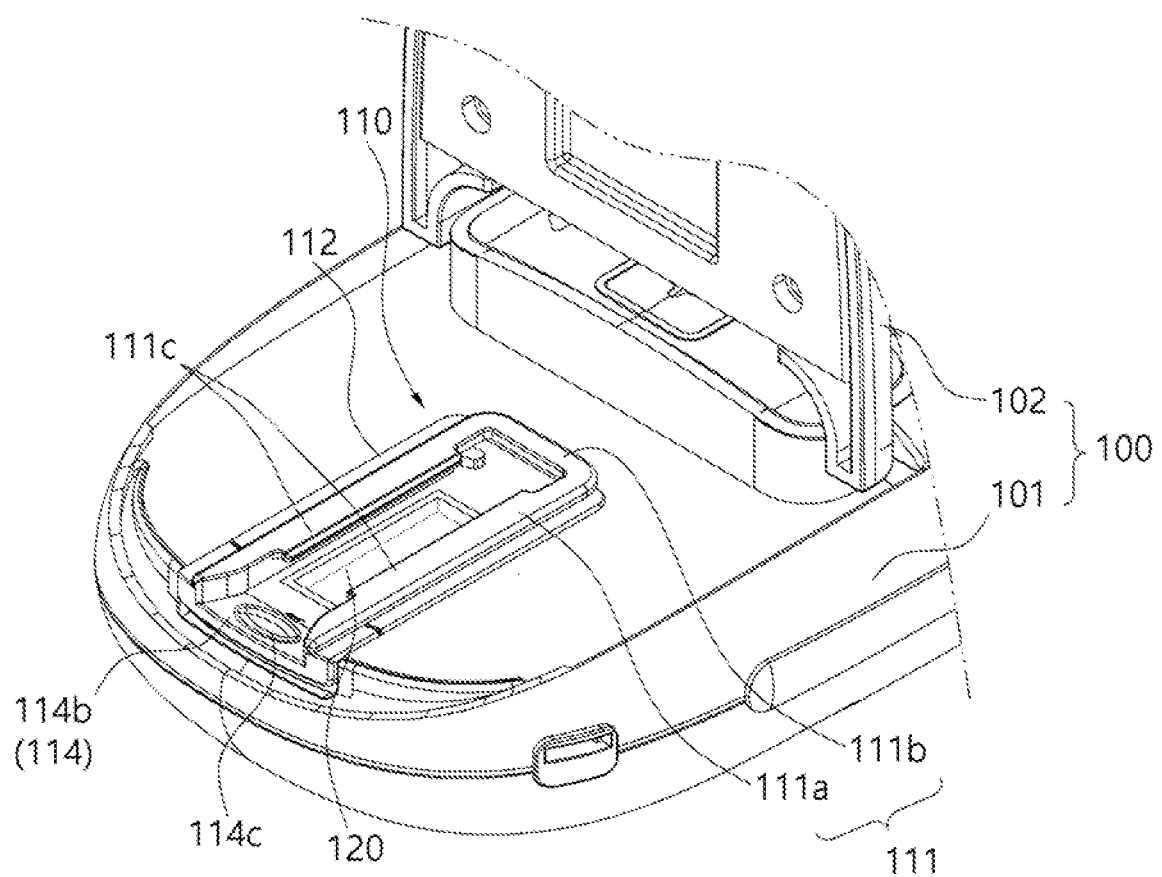
FIG. 3 is a perspective view illustrating an example in which a strip fixation unit is coupled in an embodiment of the cholesterol measurement device according to the present invention.
Figure 4:
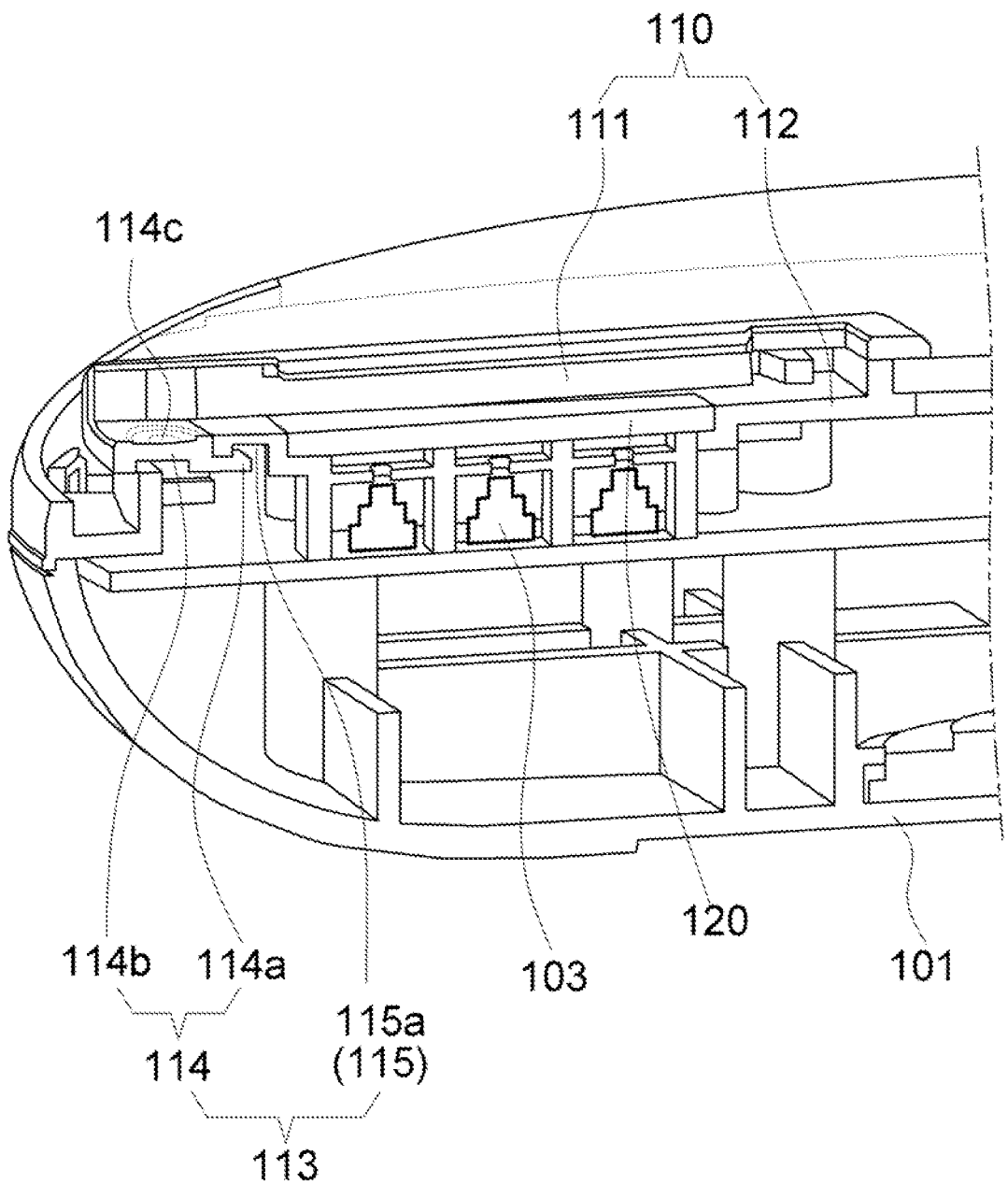
FIG. 4 is a cross-sectional view illustrating an embodiment of a measurement unit in an embodiment of the cholesterol measurement device according to the present invention.
Figure 5:
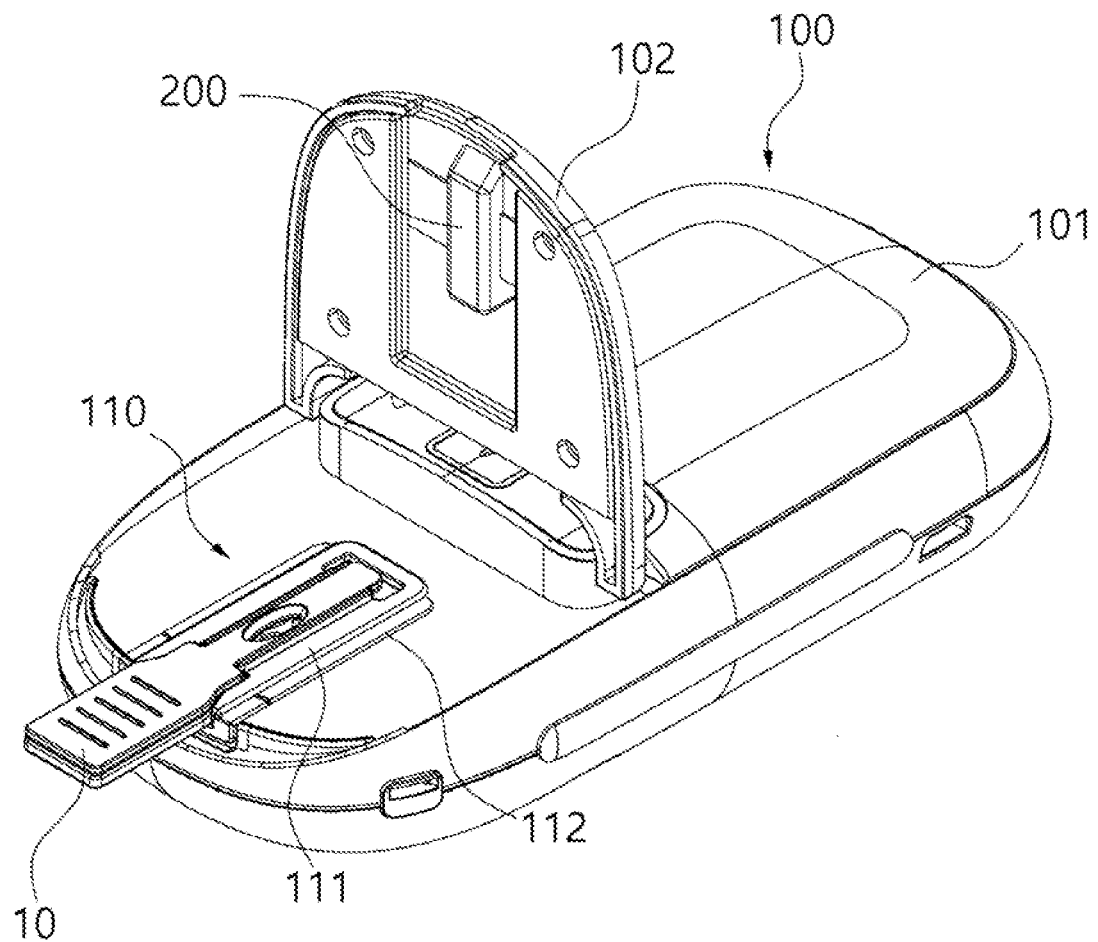
FIG. 5 is a perspective view illustrating an embodiment of the cholesterol measurement device according to the present invention.
Figure 6:
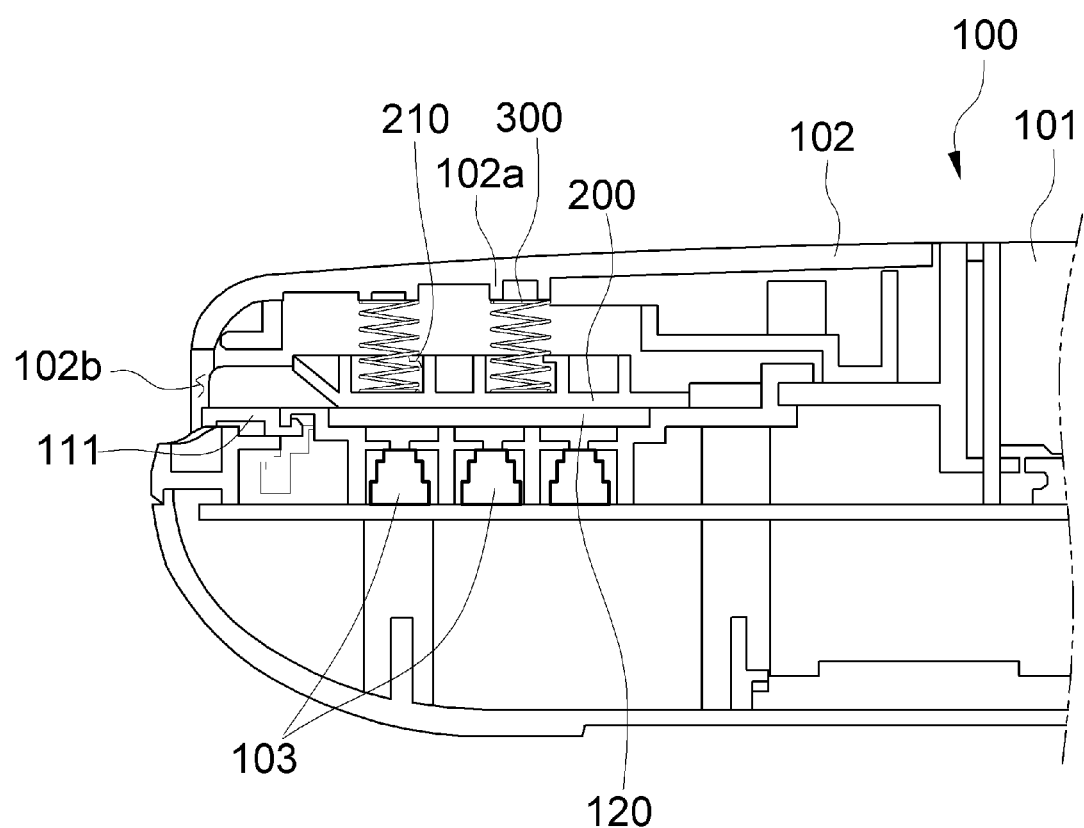
FIGS. 6 and 7 are enlarged cross-sectional views illustrating an embodiment of the cholesterol measurement device according to the present invention.
Figure 7:
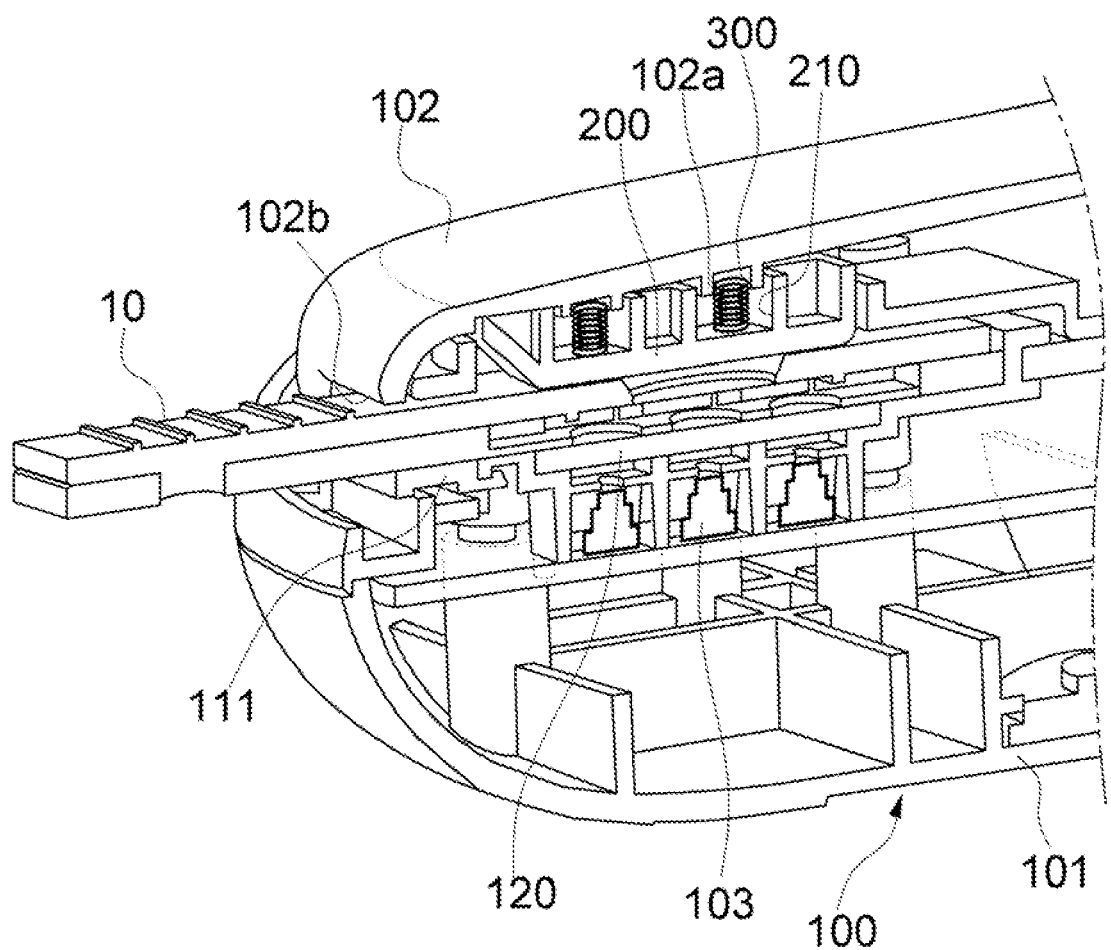

Hereinafter, the present invention will be described in detail with reference to the accompanying drawings, in which exemplary embodiments of the present invention are shown, so that the person having ordinary skill in the art to which the present invention pertains. However, the present invention may be embodied in many different forms, and is not limited to embodiments described herein. Throughout the specification, like reference numerals refer to like elements.

In addition, since respective components described in the present invention are all components capable of configuring a cholesterol measurement device of the present invention, the components may be combined without limitations regardless of positions of the components described to configure the cholesterol measurement device of the present invention.

Referring to FIGS. 1 to 7, an embodiment of a cholesterol measurement device according to the present invention includes a measurement strip 10 and a measuring instrument body 100 for measuring the quantity of cholesterol in a specimen.

The measurement strip 10 includes a specimen input unit 11 for inputting a specimen of blood or serum, and may include a specimen receiving groove for receiving the specimen. The specimen may be collected from venous blood or capillary blood of a subject to be measured, that is, a patient, or may be a serum isolated from the patient's blood.

On the upper surface of the measurement strip 10, the specimen input unit 11 is positioned to be input and stored with the specimen, and the specimen input unit 11 is formed in a groove shape with an open upper surface, so that an inspector may drop the specimen and input the specimen therein. In addition, the measurement strip 10 may further include a known configuration such as a reaction unit that reacts with the specimen.

The measuring instrument body 100 includes a body housing member 101, an opening/closing member 102, and a measurement window member 120, and the body housing member 101 includes a measurement unit 110 and a light-emitting unit 103. The measuring instrument body 100, specifically, one side of the body housing member 101 is provided with the measurement unit 110 in which the measurement strip 10 is positioned, and the light-emitting unit 103 is provided in the measuring instrument body 100 to emit light to the measurement unit 110.

The measurement unit 110 may be positioned in a recessed form on the measuring instrument body, specifically, one side of the body housing member 101, and the measurement window member 120 through which the light emitted from the light-emitting unit 103 may pass may be positioned in the measurement unit 110. The measurement window member 120 may be made of a transparent or translucent material, and may be made of various known materials through which light emitted from the light-emitting unit 103 passes.

The measurement unit 110 is provided with a strip fixation unit 111 into which the measurement strip 10 may be inserted and positioned, and the measurement window member 120 is positioned on the bottom surface at the inner part of the strip fixation unit 111 and positioned on the measurement window member 120. When the measurement strip 10 is inserted and mounted into the strip fixation unit 111, the light emitted from the light-emitting unit 103 passes through the measurement strip 10 inserted into the strip fixation unit 111 to be incident to the measurement strip 10.

The strip fixation unit 111 is positioned so that an inlet is open to one side of the body housing member 101, and the measurement strip 10 may be inserted while sliding from the inlet.

The light-emitting unit 103 is positioned inside the body housing member 101 from the lower side of the measurement window member 120 and may emit the light toward the measurement window member 120. The light-emitting unit 103 is an example of a light-emitting diode (LED), and in addition, may be variously modified and implemented into various known lamps used in a color development method that changes the color development of the measurement strip 10.

In addition, a photodiode unit (PD) for measuring light reflected from the measurement strip 10 may be positioned inside the body housing member 101. The measurement unit 110 may measure the quantity of cholesterol in the specimen using the intensity of light detected from the photo diode (PD).

The measuring instrument body 100 may measure the quantity of cholesterol in the specimen by emitting the light from the light-emitting unit 103 to emit the light to the measurement strip 10 positioned on the measurement window member 120 through the measurement window member 120 and then detecting the light reflected from the measurement strip 10 with the photo diode PD (not illustrated). This is known in the cholesterol measurement device using the color development method, and a more detailed description thereof will be omitted.

The measurement unit 110 is provided with the strip fixation unit 111 and a coupling unit for the strip fixation unit 112, the strip fixation unit 111 may be inserted with the measurement strip 10 to be detachably coupled with the measurement strip 10, and the strip fixation unit 111 may be inserted and coupled to the coupling unit for the strip fixation unit 112. The coupling unit for the strip fixation unit 112 is mounted on the measuring instrument body 100, specifically, the body housing member 101, for example, may be integrally formed with the body housing member 101.

The strip fixation unit 111 may be integrally formed with the coupling unit for the strip fixation unit 112 or may be designed to be detachable from the coupling unit for the strip fixation unit 112.

The specimen of blood or serum is dropped into the specimen inlet 11 of the measurement strip 10, and at this time, when the specimen is dropped out of the specimen inlet 111 or a dose or more of specimen is dropped to the specimen inlet 11 due to a user's mistake, the specimen contaminates the measurement unit 110.

In the case where the strip fixation unit 111 is designed to be detachably coupled to the measuring instrument body 100, specifically the body housing member 101, more particularly the coupling unit for the strip fixation unit 112, when the specimen flows into the inside of the strip fixation unit 111, the measurement unit 110 may be easily cleaned by separating the strip fixation unit 111 so that it may be expected to improve a convenience during the cleaning operation and to keep the measurement unit 110 clean at all times.

The strip fixation unit 111 may be formed in, for example, a ⊏-shape with an open inlet into which the measurement strip 10 is inserted.

For example, the strip fixation unit 111 may include strip side support members 111a which are spaced apart from each other so that the measurement strip 10 is inserted therebetween and support both sides of the measurement strip 10, and a strip front-end support member 111b which has both ends connected to one end side of the pair of strip side support members 111a spaced apart from each other, respectively, and supports the front end of the measurement strip 10.

At this time, the strip fixation unit 111 is opened in a direction of a strip inlet 102b between the strip side support members 111a, so that the measurement strip 10 may be inserted and positioned between the strip side support members 111a.

At one side of an outer side of the measurement strip 10 and an inner side of the strip side support member 111a, a first slide coupling groove 12 may be positioned, and at the other side of the outer side of the measurement strip 10 and the inner side of the strip side support member 111a, a first slide rail unit 111c inserted into the first slide coupling groove 12 may be positioned to protrude.

As an example, the first slide coupling groove 12 is formed to have an open front end in an insertion direction at both sides of the measurement strip 10. In addition, as an example, the first slide rail unit 111c is positioned on the inner side of the strip side support member 111a.

As the measurement strip 10 is inserted between the strip side support members 111a, the first slide rail unit 111c is inserted into the first slide coupling groove 12 and the measurement strip 10 slides along the first slide rail unit 111c to be coupled to the strip fixation unit 111. Further, the measurement strip 10 may be separated from the strip fixation unit 111 while sliding along the first slide rail unit 111c in a direction opposite to the insertion.

When the strip fixation unit 111 is designed to be detachable from the coupling unit for the strip fixation unit 112, the coupling unit for the strip fixation unit 112 may be formed such that the direction of the strip inlet 102b is open so that the strip fixation unit 111 may be inserted. For example, the ⊏-shaped fixation insertion space in which the direction of the strip inlet 102b is opened may be formed in the coupling unit for the strip fixation unit 112.

As an example, the coupling unit for the strip fixation unit 112 may include side support members for strip fixation unit 112a which are spaced apart from each other to support outer sides of the strip side support members 111a of the strip fixation unit 111, and a front support member for strip fixation unit 112b which supports an outer side of the strip front-end support member 111b of the strip fixation unit 111.

A second slide coupling groove 111d may be positioned at any one side of the inner side of the side support member for strip fixation unit 112a and the outer side of the strip side support member 111a, and a second slide rail unit 112c may be positioned at the other side of the inner side of the side support member for strip fixation unit 112a and the outer side of the strip side support member 111a to slide while being inserted into the second slide coupling groove 111d.

As an example, the second slide coupling groove 111d is positioned on the outer side of the strip side support member 111a, and the second slide rail unit 112c is positioned on the inner side of the side support member for strip fixation unit 112a.

The outer side of the strip side support member 111a of the strip fixation unit 111 and the inner side of the side support member for strip fixation unit 112a of the coupling unit for the strip fixation unit 112 may have a spacing of at least 0.01 mm to 2.0 mm, preferably 0.1 mm to 1.5 mm, more preferably 0.3 mm to 1.0 mm.

When the measurement strip 10 is inserted into the strip fixation unit 111, the spacing may be filled by the outer side modified by elastically modifying the strip side support member 111a.

A width of the measurement strip 10 may be formed to be larger than a spacing between the inner sides of the corresponding strip side support members by 0.02 mm to 4.0 mm, preferably 0.2 mm to 3.0 mm, more preferably 0.6 mm to 2.0 mm.

In the conventional cholesterol measurement device, since the spacing is not formed, the modification of the strip fixation unit is likely to occur, and when such a modification of the strip fixation unit occurs, there is a problem in that the fixing position of the measurement strip is changed. That is, when the fixing position of the measurement strip is changed as described above, since a cholesterol measurement value is also changed, this problem acts as a cause that makes it difficult to accurately measure cholesterol.

However, the structure as described above of the present invention forms a space between the outer side of the strip side support member 111a of the strip fixation unit 11 and the inner side of the side support member for strip fixation unit 112a of the coupling unit for the strip fixation unit 112 to prevent the modification of the strip fixation unit 111. When the measurement strip 10 is inserted into the strip fixation unit 111, the space is configured to be filled by the outer side of the strip side support member 111a while being elastically modified to perform the cholesterol measurement under predetermined conditions, thereby improving the accuracy of the cholesterol measurement.

A coupling guide groove 111e may be positioned on any one side of the inner side of the front support member for strip fixation unit 112b of the coupling unit for the strip fixation unit 112 and the outer side of the strip front-end support member 111b, and a coupling guide rail unit 112d inserted into the coupling guide groove 111e may be positioned to protrude from the other side of the inner side of the front support member for strip fixation unit 112b and the outer side of the strip front-end support member 111b.

For example, the coupling guide groove 111e is positioned on the outer side of the strip front-end support member 111b, and the coupling guide rail unit 112d is positioned on the inner side of the front support member for strip fixation unit 112b.

The coupling unit for the strip fixation unit 112 may further include a strip fixation unit coupling checking switch (112e in FIG. 2) which is pressed when the strip fixation unit 111 is inserted, and installed to check whether the strip fixation unit is coupled.

The measurement unit 110 may further include a fixation locking unit 113 capable of locking the position of the strip fixation unit 111 coupled to the coupling unit for the strip fixation unit 112.

The fixation locking unit 113 may include a first locking unit 114 positioned at a rear end side of the strip fixation unit 111 and a second locking unit 115 positioned at the rear end side of the coupling unit for the strip fixation unit 112 and positioned and locked with the first locking unit 114.

The second locking unit 115 includes a locking groove 115a formed on a lower surface from the rear end side of the coupling unit for the strip fixation unit 112, and the first locking unit 114 may include a wedge-shaped locking step 114a which is inserted to the locking groove 115a at an end side thereof.

In addition, the first locking unit 114 may include an elastic support member 114b that elastically supports and presses the locking step 114a to separate the locking step 114a from the locking groove 115a.

As an example, the elastic support member 114b is positioned at the other end side of the pair of strip side support members 111a spaced apart from each other so that both ends thereof are connected to each other.

On an upper surface of the elastic support member 114b, a pressing groove 114c indicating a pressing position of the elastic support member 114b may be positioned.

The elastic support member 114b descends when a portion where the pressing groove 114c is positioned is pressed so that the locking step 114a may be separated from the locking groove 115a.

The strip fixation unit 111 is pulled to the rear side while the elastic support member 114b is pressed and the locking step 114a is separated from the locking groove 115a to be separated from the coupling unit for the strip fixation unit 112.

That is, the strip fixation unit 111 is inserted into a fixation insertion space, and slides to be coupled to the coupling unit for the strip fixation unit 112 until the coupling guide rail unit 112d is inserted into the coupling guide groove 111e while the second slide rail unit 112c is inserted into the second slide coupling groove 111d and slides.

At this time, the elastic support member 114b may be locked when the wedge-shaped locking step 114a is naturally inserted into the locking groove 115a.

When pressing the portion where the pressing groove 114c is positioned in the elastic support member 114b, the locking step 114a is separated from the locking groove 115a, and while the locking step 114a is separated from the locking groove 115a, when the strip fixation unit 111 is pulled toward the rear side of the fixation insertion space, the strip fixation unit 111 may be simply separated from the coupling unit for the strip fixation unit 112.

The measuring instrument body 100 may further include a light-intensity check member 200 which reflects the light emitted from the light-emitting unit 103 to check whether the intensity of light is abnormal. In this case, the light-intensity check member 200 may be mounted and provided integrally with the measuring instrument body 100, specifically the opening/closing member 102.

The opening/closing member 102 may open and close the measurement unit 110 and may be rotatably coupled to the body housing member 101. As an example, the opening/closing member 102 is rotatably coupled to the body housing member 101 with a hinge portion and rotated around the hinge portion to open and close the measurement unit 110.

The opening/closing member 102 has a size and a shape capable of covering the measurement unit 110 and may be formed to have a height corresponding to the height of the recessed measurement unit 110.

The light-intensity check member 200 reflects the light emitted through the light-emitting unit 103 so as to check the light intensity of the light-emitting unit 103. The light-intensity check member 200 may be positioned on the lower surface of the opening/closing member 102, and is positioned to correspond to the measurement window member 120 when the opening/closing member 102 is closed so that the light of the light-emitting unit 103 passing through the measurement window member 120 may be emitted.

As an example, the light-intensity check member 200 has a specific gray value capable of measuring the intensity of LED light by reflection, and in addition, the light-intensity check member 200 may be modified into a variety of known colors so as to measure the intensity of light by reflecting the light emitted from the light-emitting unit 103.

The measuring instrument body 100 may further include a spring member 300, and the spring member 300 is positioned between the light-intensity check member 200 and the opening/closing member 102 so that the light-intensity check member 200 may be in close contact with the measurement window member 120 in the state where the opening/closing member 102 is closed.

As an example, the spring member 300 is a coil spring, and a portion of the lower end side of the spring member 300 may be coupled to the upper surface of the light-intensity check member 200. For example, a plurality of spring insertion units 210 for guiding a vertical movement of the spring member 300 may be provided on the upper surface of the light-intensity check member 200, and in this case, the spring member 300 may be inserted and positioned into the spring insertion units 210. For example, the plurality of spring insertion units 210 may be partitioned by a plurality of partition walls formed on the upper surface of the light-intensity check member 200, and the plurality of partition walls may be spaced apart from each other to guide the vertical movement of the spring member 300.

Further, a plurality of spring fitting units 102a into which a portion of the upper end side of the spring member 300 is fitted may be positioned on the lower surface of the opening/closing member 102.

An upper end side of the spring member 300 is fitted and coupled into the spring fitting unit 102a, and a portion at the lower end side of the spring member 300 is inserted into the spring insertion units 210 so that restoration by compression and elastic restoring force may be stably repeated.

As an example, the light-intensity check member 200 may be formed in a block shape having a flat lower surface that may be in close contact with the measurement window member 120 and has an area covering the front surface of the measurement window member 120.

The block shape has the flat lower surface that may be in close contact with the measurement window member 120, and is not particularly limited so long as the shape is a shape capable of measuring the intensity of light by uniformly reflecting the light emitted from the light-emitting unit 103. Specifically, for example, plate shapes such as a square plate, polygonal column shapes such as a square column shape, etc. may be included. In the case of the polygonal column shape, the direction of the lower surface of the opening/closing member 102 may be opened so that the spring may be stably interposed therebetween.

In the state where the opening/closing member 102 is closed, the light-intensity check member 200 is elastically supported by the spring member 300 to be positioned in close contact with the measurement window member 120, thereby accurately measuring the light intensity of the light-emitting unit 103. In addition, the measurement strip 10 comes into close contact with the measurement window member 120 and the position of the measurement strip 10 is fixed by pressing the measurement strip 10 positioned on the measurement window member 120, thereby more stably and accurately measuring the quantity of cholesterol.

At one side of the opening/closing member 102, the strip inlet 102b may be positioned to be opened so that the measurement strip 10 passes through the strip inlet 102b to be inserted between the light-intensity check member 200 and the measurement window member 120.

The strip inlet 102b is positioned to coincide with the opened inlet at the rear side of the strip fixation unit 111 and the measurement strip 10 is inserted into the strip fixation unit 111 through the inlet of the strip fixation unit 111 and the strip inlet 102b in the state where the opening/closing member 102 is closed to be positioned between the light-intensity check member 200 and the measurement window member 120.

The light-intensity check member 200 may have an inclined surface capable of guiding the insertion of the measurement strip 10 at the front end side positioned toward the strip inlet 102b.

When the measurement strip 10 is inserted into the strip fixation unit 111 through the inlet of the strip fixation unit 111 and the strip inlet 102b in the state where the opening/closing member 102 is closed, the light-intensity check member 200 elevates while compressing the spring member 300 to insert the measurement strip 10 into the strip fixation unit 111.

The light-intensity check member 200 may naturally elevate while the end side of the measurement strip 10 is inserted while pushing the inclined surface to insert and position the measurement strip 10 into the strip fixation unit 111.

That is, even while the opening/closing member 102 is closed, the measurement strip 10 may be positioned into the strip fixation unit 111, and the measurement strip 10 positioned into the strip fixation unit 111 may be pressed by the block-shaped light-intensity check member 200 to be stably positioned while coming into close contact with the measurement window member 120 in the measurement insertion unit.

Meanwhile, the cholesterol measurement device according to the present invention may include a light-intensity abnormality checking unit (not illustrated) which operates the light-emitting unit 103 to emit the light to the light-intensity check member 200 and checks whether the light-emitting unit 103 is abnormal, that is, whether the intensity of light is abnormal by the light reflected by the light-intensity check member 200.

The light-intensity abnormality checking unit may operate the light-emitting unit 103 to emit the light to the light-intensity check member 200 before the light-intensity check member 200 is in close contact with the measurement window member 120, that is, the measurement strip 10 is inserted and coupled to the strip fixation unit 111 and check whether the light-emitting unit 103 is abnormal, that is, whether the intensity of light is abnormal by the light reflected by the light-intensity check member 200.

Meanwhile, the measuring instrument body 100 includes a real time clock (RTC), and the light-intensity abnormality checking unit (not illustrated) may check whether a date has changed when power is turned ON, operate the light-emitting unit 103 when the date is changed to emit the light to the light-intensity check member 200, and check whether the light-emitting unit 103 is abnormal, that is, whether the intensity of light is abnormal by the light reflected by the light-intensity check member 200.

The light-intensity abnormality checking unit may first operate the light-emitting unit 103 when the power of the measuring instrument body 100 is turned on to emit the light to the light-intensity check member 200, measure a reflection value reflected by the light-intensity check member 200, and store an initial reflection value.

In addition, when the power is repeatedly turned on for the use of the measuring instrument body 100, the light-intensity abnormality checking unit may check the date with the RTC whenever the power is turned on, operate the light-emitting unit 103 when the date is changed to emit the light to the light-intensity check member 200, and check whether the light intensity of the light-emitting unit 103 is abnormal by compare the reflection value reflected by the light-intensity check member 200 with the initial reflection value.

In addition, the light-intensity abnormality checking unit includes a light-intensity abnormality notification unit that notifies the outside when it is checked that the light intensity of the light-emitting unit 103 is abnormal to re-control the light intensity of the light-emitting unit 103.

That is, while the light-intensity check member 200 is maintained in a state that is always mounted on the measuring instrument body 100 and the opening/closing member 102 is closed, when the power of the measuring instrument body 100 is turned on, the light-intensity abnormality checking unit automatically checks whether the light intensity of the light-emitting unit 103 is abnormal, thereby securing the accuracy and reliability of the cholesterol measurement.

The light-intensity check member 200 is provided integrally with the measuring instrument body 100 by changing the check strip of checking whether the light intensity is abnormal into the block shape to have no fear of loss and solve an inconvenience to store the check strip separately, thereby improving a convenience in use.

When the light-intensity check member 200 inspects whether the light intensity is abnormal, it is possible to solve the problems caused by a deviation in the check strip, accurately confirm a change in light intensity to prevent a change in measurement value according to the change in light intensity, and improve the reliability to the measurement value.

The light-intensity abnormality checking unit automatically checks everyday whether the light intensity is abnormal to ensure the accuracy and reliability for cholesterol measurement.

Figure 8:
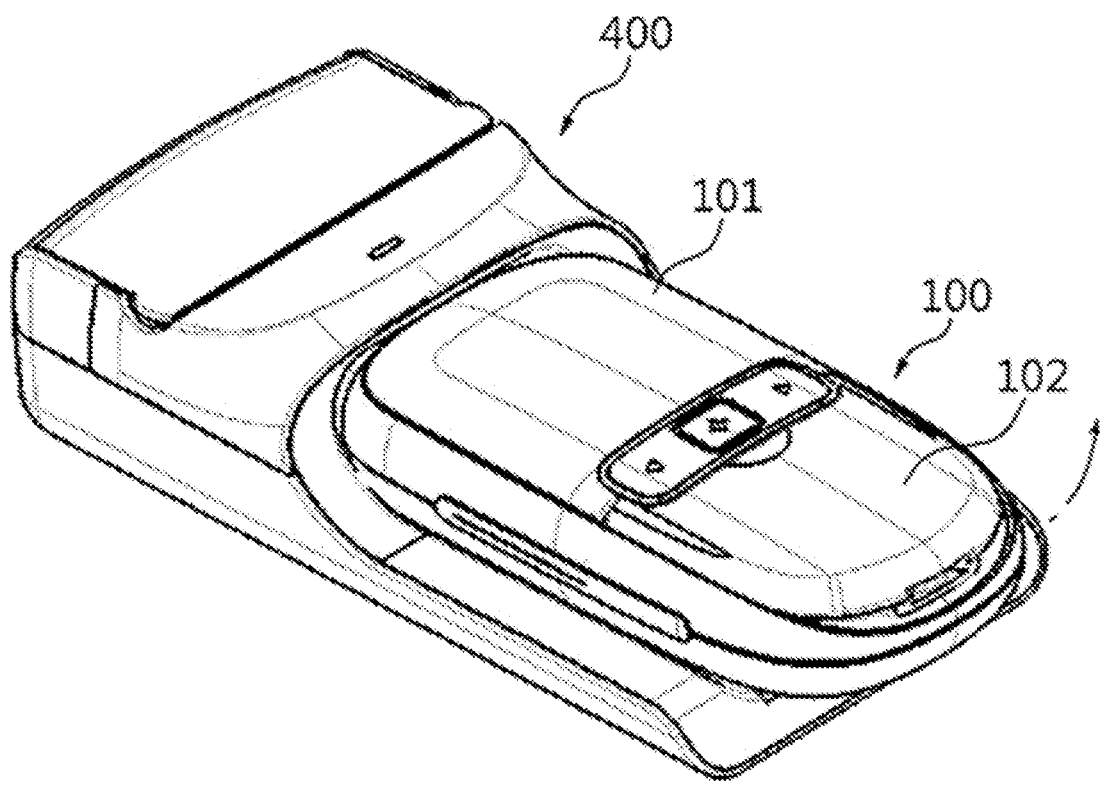
FIG. 8 is a perspective view illustrating another embodiment of a cholesterol measurement device according to the present invention.
Figure 9:
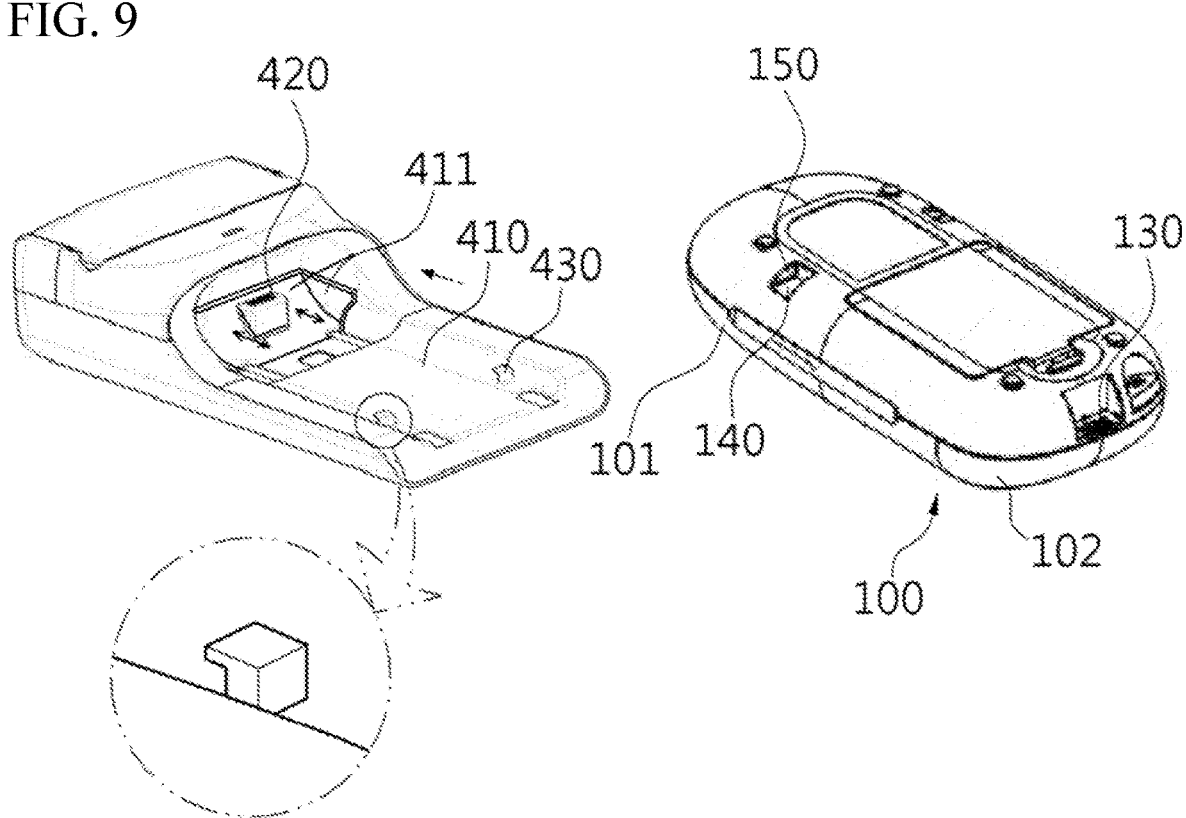
FIG. 9 is an exploded perspective view illustrating another embodiment of the cholesterol measurement device according to the present invention.

FIG. 8 is a perspective view illustrating another embodiment of a cholesterol measurement device according to the present invention and FIG. 9 is an exploded perspective view illustrating another embodiment of the cholesterol measurement device according to the present invention.

Referring to FIGS. 8 and 9, the cholesterol measurement device according to the present invention may further include a printer body 400 which is detachably coupled with the measuring instrument body 100 and electrically connected with the measuring instrument body 100 to print a result of cholesterol measurement values measured by the measuring instrument body 100.

The printer body 400 may include a printer unit which receives the result of the cholesterol measurement values measured by the measuring instrument body 100 and outputs the result on paper, and a rechargeable battery that supplies electric power to the printer unit.

The printer unit is a known configuration in a known printer device, and a more detailed description thereof will be omitted.

In the printer body 400, a charging terminal (not illustrated) which is connected with a charging cable to charge the rechargeable battery is positioned, and the charging terminal may be variously modified and implemented using known terminals such as a USB terminal, a micro 5-pin terminal, etc.

The printer body 400 may be used even while carrying by including the rechargeable battery, and may output the result of the cholesterol measurement values easily even in places where power connection is disabled.

In the printer body 400, a measuring instrument seating unit 410 on which the measuring instrument body 100 is seated is positioned, and in the measuring instrument seating unit 410, a measuring instrument connection terminal unit 420 may be positioned to be electrically connected with the measuring instrument body 100 seated in the measuring instrument seating unit 410.

In addition, in the measuring instrument body 100, a printer connection terminal unit 130 may be positioned to be electrically connected to the measuring instrument connection terminal unit 420 to be electrically connected with the printer body 400.

When the measuring instrument body 100 is seated on the measuring instrument seating unit 410, the printer connection terminal unit 130 is connected with the measuring instrument connection terminal unit 420 to be electrically connected with the measuring instrument body 100, the printer body 400 may receive and output the result of the cholesterol measurement values from the measuring instrument body 100.

In the measuring instrument seating unit 410, a locking member 430 for locking and fixing the measuring instrument body 100 is positioned to protrude, and on the lower surface of the measuring instrument body 100, the first locking insertion unit 140 into which the locking member 430 is inserted and locked may be positioned.

The locking member 430 has a ¬-shaped shape and is positioned to protrude on the measuring instrument seating unit 410, and a second locking insertion unit 150 into which a bent end side of the locking member 430 is inserted may be positioned in the first locking insertion unit 140.

In addition, in the measuring instrument seating unit 410, a moving member 411 may be positioned to support the rear end of the measuring instrument body 100 and be pushed toward the rear end of the measuring instrument body 100, and be elastically supported to return to its original position.

The moving member 411 is moved to the rear side of the measuring instrument body 100 while the measuring instrument body 100 is positioned on the measuring instrument seating unit 410 so that the locking member 430 may be removed and separated from the first locking insertion unit 140.

The locking member 430 may be positioned such that the ¬-shaped bent end side faces the rear side, and the second locking insertion unit 150 may be positioned on the rear surface in the first locking insertion unit 140.

In addition, as an example, the printer connection terminal unit 130 is positioned at the front end side from the lower surface of the measuring instrument body 100, and the measuring instrument connection terminal unit 420 is positioned at a moving unit.

The measuring instrument body 100 is seated on the measuring instrument seating unit 410 so that while the printer connection terminal unit 130 and the measuring instrument connection terminal unit 420 are electrically connected to each other, the end portion that is bent while the locking member 430 is inserted into the first locking insertion unit 140 is inserted and locked into the second locking insertion unit 150 to be coupled with the printer body 400.

That is, while the measuring instrument body 100 is seated on the measuring instrument seating unit 410, the end portion that is bent while the locking member 430 is inserted into the first locking insertion unit 140 is inserted and locked into the second locking insertion unit 150 to be firmly coupled with the printer body 400 and to be prevented from being separated.

In addition, when the measuring instrument body 100 is separated from the printer body 400, the measuring instrument body 100 is pushed to the rear side, the moving member 411 moves to the rear side, and then the bent end portion of the locking member 430 inserted into the second locking insertion unit 150 is removed from the locking insertion unit 150 to be easily separated from the printer body 400 by lifting the measuring instrument body 100.

According to the present invention, it is possible to have no fear of loss and solve an inconvenience to store a check strip separately to improve convenience in use by changing a check strip of confirming whether the quality of light is abnormal into a block shape to be provided integrally with the measuring instrument body 100.

According to the present invention, it is possible to solve the problems caused by a deviation in a check strip when the light-intensity check member 200 of confirming whether the quality of LED light is abnormal is integrally provided to inspect whether the light quality is abnormal, accurately confirm a change in light intensity to prevent a change in measurement value according to the change in light intensity, and improve the reliability to the measurement value.

According to the present invention, it is possible to ensure the accuracy and reliability for cholesterol measurement by automatically confirming everyday whether the light intensity is abnormal.

According to the present invention, it is possible to greatly improve a convenience in use by including a printer which is detachable from the measuring instrument body 100 and portable to output a measurement value directly in use and confirm the measurement value.

According to the present invention, it is possible to improve a convenience during cleaning and keep the measurement unit clean at all times by separating the strip fixation unit when a specimen flows into the strip fixation unit into which the measurement strip is inserted to easily clean the measurement unit.

According to the present invention, it is possible to improve the accuracy of the measurement value when measuring cholesterol and secure the reliability of the measurement value by easily cleaning the measurement unit.

According to the present invention, it is possible to greatly improve a convenience in use by including a printer which is detachable from the measuring instrument body and portable to output a measurement value directly in use and confirm the measurement value.

While the preferred embodiment of the present invention has been described in detail, the scope of the present invention is not limited thereto, and various modifications and variations of those skilled in the art using basic concepts of the present invention which have been defined in the appended claims cover the scope of the present invention.

EXPLANATION OF REFERENCE NUMERALS AND SYMBOLS

10: Measurement strip
11: Specimen input unit
12: First slide coupling groove
100: Measuring instrument body
101: Body housing member
102: Opening/closing member
103: Light-emitting unit
102a: Spring fitting unit
102b: Strip inlet
110: Measurement unit
111: Strip fixation unit
111a: Strip side support member
111b: Strip front-end support member
111c: First slide rail unit
111d: Second slide coupling groove 12: Coupling unit for the strip fixation unit
12a: Side support member for strip fixation unit
12b: Front support member for strip fixation unit
112c: Second slide rail unit
2d: Coupling guide rail unit
112e: Strip fixation unit coupling checking switch
113: Fixation locking unit
114: First locking unit
114a: Locking step
114b: Elastic support member
114c: Pressing groove
115: Second locking unit
115a: Locking groove
120: Measurement window member
130: Printer connection terminal unit
140: First locking insertion unit
150: Second locking insertion unit
200: Light-intensity check member
210: Spring insertion unit
300: Spring member
400: Printer body
410: Measuring instrument seating unit
411: Moving member
420: Measuring instrument connection terminal unit
430: Locking member

The invention claimed is:

1. A cholesterol measurement device comprising:
a measuring instrument body which includes a measurement unit where a measurement strip is positioned and a light-emitting unit emitting light to the measurement unit and detects the intensity of light reflecting with a photo diode after emitting the light to the measurement strip to measure the quantity of cholesterol; and
a light-intensity check member for reflecting light emitted from the light-emitting unit to check whether the intensity of light is abnormal, said light-intensity check member being mounted and integrally provided on the measuring instrument body;
wherein the measuring instrument body includes
a body housing member of which the measurement unit where the measurement strip is positioned is provided at one side and the light-emitting unit emitting the light to the measurement unit is provided therein; and
an opening/closing member opening and closing the measurement unit, wherein the light-intensity check member is positioned on a lower surface of the opening/closing member,
wherein a measurement window member through which the light emitted from the light-emitting
unit passes is positioned in the measurement unit, and the light-intensity check member is elastically supported by a spring member in the state where the opening/closing member is closed, and is positioned in close contact with the measurement window member,
wherein a strip inlet is positioned at one side of the opening/closing member so that the measurement strip can be inserted between the light-intensity check member and the measurement window member in the state where the opening/closing member is closed, and
the light-intensity check member has a block shape having a flat lower surface and has an inclined surface which is positioned at a front end side positioned toward the strip inlet to guide the insertion of the measurement strip.

2. The cholesterol measurement device of claim 1, wherein the measuring instrument body includes a real time clock (RTC), and includes a light-intensity abnormality checking unit which checks whether a date has changed when power is turned ON, operates the light-emitting unit when the date is changed to emit the light to the light-intensity check member, and checks whether the light-emitting unit is abnormal by the light reflected by the light-intensity check member.

3. The cholesterol measurement device of claim 1, wherein the measurement unit includes a strip fixation unit to which the measurement strip is inserted and detachably coupled, which is detachable from the measuring instrument body; and a coupling unit for the strip fixation unit which is mounted and positioned on the measuring instrument body and is detachably coupled with the strip fixation unit; wherein the measurement unit is capable of cleaning.

4. The cholesterol measurement device of claim 3, wherein the strip fixation unit includes
strip side support members which are spaced apart from each other so that the measurement strip is inserted therebetween and support both sides of the measurement strip; and
a strip front-end support member which has both end sides which are connected to one end side of the pair of the spaced strip side support members and supports a front-end of the measurement strip,
wherein a first slide coupling groove is positioned in a longitudinal direction at any one side of an outer side of the measurement strip and an inner side of the strip side support member, and a first slide rail unit inserted into the first slide coupling groove is positioned to protrude at the other side of the outer side of the measurement strip and the inner side of the strip side support member.

5. The cholesterol measurement device of claim 4, wherein the coupling unit for the strip fixation unit includes
side support members for strip fixation unit spaced apart from each other to support the outer sides of the strip side support members of the strip fixation unit; and a front support member for strip fixation unit supporting the outer side of the strip front-end support member,
wherein a second slide coupling groove is positioned at any one side of an inner side of the side support member for strip fixation unit and an outer side of the strip side support member, and a second slide rail unit is positioned at the other side of the inner side of the side support member for strip fixation unit and the outer side of the strip side support member to be inserted into the second slide coupling groove and slides.

6. The cholesterol measurement device of claim 5, wherein the outer side of the strip side support member of the strip fixation unit and the inner side of the side support member for strip fixation unit of the coupling unit for the strip fixation unit have a spacing of at least 0.01 mm to 2.0 mm, and
the spacing is filled by the outer side of the strip side support member while the strip side support member is elastically modified when the measurement strip is inserted into the strip fixation unit.

7. The cholesterol measurement device of claim 5, wherein a coupling guide groove is positioned at any one side of the inner side of the front support member for strip fixation unit of the coupling unit for the strip fixation unit and the outer side of the strip front-end support member of the strip fixation unit, and a coupling guide rail unit inserted into the coupling guide groove is positioned to protrude at the other side of the inner side of the front support member for strip fixation unit and the outer side of the strip front-end support member.

8. The cholesterol measurement device of claim 3, wherein the measurement unit further includes a fixation locking unit capable of locking the position of the strip fixation unit coupled to the coupling unit for the strip fixation unit.

9. The cholesterol measurement device of claim 8, wherein the fixation locking unit includes
- a first locking unit positioned at the rear end side of the strip fixation unit; and
- a second locking unit positioned at the rear end side of the coupling unit for the strip fixation unit and positioned to be locked with the first locking unit.

10. The cholesterol measurement device of claim 1, wherein the cholesterol measurement device further comprises a printer body which is detachably coupled with the measuring instrument body and electrically connected with the measuring instrument body to print a result of cholesterol measurement values measured by the measuring instrument body and is embedded with a rechargeable battery.

11. The cholesterol measurement device of claim 10, wherein the printer body comprises a measuring instrument seating unit on which the locking member for locking and fixing the measuring instrument body is positioned to protrude,
- wherein the locking member has a L-shaped hook so that a bent end side of the L-shaped hook is positioned at the rear side and the measuring instrument body includes a first locking insertion unit on the lower surface into which the locking member is inserted and locked,
- wherein the first locking insertion unit includes a second locking insertion unit into which the bent end side of the locking member is inserted, and
- wherein the measuring instrument seating unit includes a portion adapted to support the rear end of the measuring instrument body and be elastically supported to return to its original position.

* * * * *